United States Patent [19]

Weinstein et al.

[11] Patent Number: 5,370,660
[45] Date of Patent: Dec. 6, 1994

[54] APPARATUS AND METHOD FOR DELIVERING A VESSEL PLUG INTO THE BODY OF A PATIENT

[75] Inventors: Lawrence A. Weinstein, Davie, Fla.; Richard A. Hillstead, Duluth, Ga.

[73] Assignee: Cordis Corporation, Miami Lakes, Fla.

[21] Appl. No.: 145,965

[22] Filed: Nov. 1, 1993

[51] Int. Cl.⁵ .............................. A61B 17/04
[52] U.S. Cl. ....................... 606/215; 606/213; 604/15
[58] Field of Search ............ 606/213, 215, 216, 251; 604/15, 60, 285, 288

[56] References Cited

U.S. PATENT DOCUMENTS

| | | | |
|---|---|---|---|
| 4,744,364 | 5/1988 | Kensey | 606/213 |
| 4,838,280 | 6/1989 | Haaga | 128/751 |
| 4,852,568 | 8/1989 | Kensey | 606/213 |
| 4,885,003 | 12/1989 | Hillstead | 604/22 |
| 4,890,612 | 1/1990 | Kensey | 606/213 |
| 4,900,303 | 2/1990 | Lemelson | 604/54 |
| 4,921,484 | 5/1990 | Hillstead | 604/104 |
| 4,929,246 | 5/1990 | Sinofsky | 606/8 |
| 5,021,059 | 6/1991 | Kensey et al. | 606/213 |
| 5,053,046 | 10/1991 | Janese | 606/213 |
| 5,061,274 | 10/1991 | Kensey | 606/213 |
| 5,108,421 | 4/1992 | Fowler | 606/213 |
| 5,116,357 | 5/1992 | Eberbach | 606/213 |
| 5,129,882 | 7/1992 | Weldon et al. | 604/96 |
| 5,149,331 | 9/1992 | Ferdman et al. | 604/290 |
| 5,221,259 | 6/1993 | Weldon et al. | 604/96 |
| 5,222,974 | 6/1993 | Kensey et al. | 606/213 |

FOREIGN PATENT DOCUMENTS

0482350A2  4/1992  European Pat. Off.
WO90/14796  12/1990  WIPO
WO92/22252  12/1992  WIPO Primary Examiner—Stephen C. Pellegrino
Assistant Examiner—Gary Jackson
Attorney, Agent, or Firm—Lockwood, Alex, Fitzgibbon & Cummings

[57] ABSTRACT

An apparatus and method for delivering a vessel plug into a wound or incision in a living patient are described. The apparatus includes an expandable porous mesh mounted at the distal end of an elongate catheter. The expandable mesh may be positioned within a blood vessel or a target organ and expanded. When the mesh member is in an expanded condition, the mesh can be positioned adjacent the opening within the vessel or organ and a vessel plug can be inserted into the wound. The expanded mesh prevents the advancement of the vessel plug into the vessel or target organ, thereby avoiding possible thrombosis or stenosis within the vessel at the wound or incision site. Occlusion of the blood vessel during treatment is avoided by providing the expandable mesh with a porous construction which allows blood or other body fluids to flow therethrough while the apparatus is being used within the body of the patient. Non-thrombogenic materials can be used to treat the apparatus to prevent significant coagulation on the device during its use.

18 Claims, 2 Drawing Sheets

APPARATUS AND METHOD FOR DELIVERING A VESSEL PLUG INTO THE BODY OF A PATIENT

The present invention generally relates to a hemostatic device and to a method for its use and, more specifically, to an apparatus enabling the placement of a vessel plug within a wound to seal the wound while simultaneously preventing the plug from entering and thereby occluding the blood vessel.

BACKGROUND AND BRIEF DESCRIPTION OF THE INVENTION

Medical procedures such as balloon angioplasty and other catheterization procedures require the insertion of an instrument into a blood vessel through a conventional catheter introducer. When inserted within the blood vessel, the catheter and the catheter introducer are manipulated by the physician or other qualified medical personnel in a manner which can cause further enlargement of the incision. The specific size of the opening can vary depending upon the type of procedure and the size of the catheter used. But, regardless of the size of the catheter, some bleeding is usually associated with the removal of the device from the blood vessel. Bleeding from the wound can be more severe for some patients and the application of external pressure to the incision may not be sufficient to prevent a hematoma or an unsightly bruise.

Various devices and procedures have been proposed to resolve the above-discussed problem. In use, these devices are typically inserted into the incision or wound to dispense a clotting agent or a closure member. While it is generally preferred that at least the distal portion of the device extends into the blood vessel, the use of such prior art devices has resulted in at least a partial occlusion the vessel during the procedure. In some devices, the vessel remains at least partially occluded even after the device is withdrawn.

Several prior art devices dispense an expandable closure member or plug directly into the blood vessel. The closure member is affixed to a filament or suture which is used to secure the closure member against the inner surface of the blood vessel at the puncture sight to thereby seal the vessel and prevent further bleeding. Such closure members, however, are typically positioned within the vessel in a manner which results in the closure member not being contiguous with the inner lumen of the blood vessel and, consequently, the closure member can partially occlude the blood flowing through that area of the vessel. A potentially serious consequence of this is the deposition of plaque and thrombus formation. By way of example, the use of closure members or plugs is shown in U.S. Pat. Nos. 4,744,364; 4,890,612; and 5,061,274 to Kensey and U.S. Pat. No. 5,021,059 to Kensey et al.

Other devices dispense a clotting agent into the wound area. However, the clotting agent is typically dispensed as a viscous liquid which then must solidify. When in a liquid state, the clotting agent is capable of entering the blood vessel. Possible stenosis can result should the clotting agent solidify with a portion thereof protruding into the blood vessel. The use of clotting agents is exemplified in U.S. Pat. Nos. 5,129,882 and 5,221,259 to Weldon et al.

Other devices have attempted to prevent the intrusion of the clotting agent or plug into the blood vessel by providing a device adapted to partially extend into the blood vessel to form a surface contiguous with the inner lumen of the vessel around the incision. A vessel plug can be inserted into the wound the device prevents the overadvancement of the vessel plug into the blood vessel. One problem of such a device, however, has been that the portion of the device positioned within the vessel will at least partially occlude blood flow while the vessel plug is being positioned within the wound. Exemplary of such a device is that disclosed in U.S. Pat. No. 5,108,421 to Fowler.

The art has generally failed to provide an apparatus which effectively closes a puncture in the wall of the blood vessel and which also avoids occluding the vessel either by the device itself when in use or by the vessel plug or other material used to seal the wound. The present invention overcomes the aforementioned problems and shortcomings of the prior art by providing an apparatus and a method for inserting a vessel plug into a wound or incision wherein neither the apparatus nor the plug significantly interferes with the flow of blood through the vessel.

The apparatus of the present invention includes an expandable porous mesh mounted at the distal end of an elongate catheter or shaft. The apparatus is configured for insertion into a wound or incision through a sheath introducer to properly position the expandable mesh within the blood vessel or target organ. A control wire is connected to an inner surface of the expandable mesh and extends through the attached catheter where it is connected to a suitable actuating mechanism. The device is constructed so that a pulling force exerted on the control wire will cause the mesh to expand. The device can then be positioned in the wound with the expanded mesh against the inner surface of the blood vessel and contiguous with the wound or opening therein. A clotting agent or vessel plug is inserted in the wound and advanced along the shaft up to the expanded mesh. The mesh prevents the further advancement of the plug so that the distal end of the plug is substantially coextensive with the inner lumen of the vessel, thereby avoiding intrusion of the plug into the blood vessel. Once the plug is in place, the mesh can be relaxed again to assume a narrow profile and the apparatus can be removed while the plug remains in the incision to prevent additional bleeding and assist in coagulation.

The expandable mesh is manufactured with a porous network of fibers which allow blood to flow therethrough while the apparatus is positioned within the blood vessel. Additionally, the expandable mesh and the attached catheter may be treated with a non-thrombogenic substance to prevent significant clotting along the device and to permit free movement of the device within the plug after coagulation has started. Once the device is removed from the vessel, the plug will permit coagulation to take place at the puncture site while avoiding possible stenosis or thrombus formation which might result if the plug were to protrude into the vessel.

It is accordingly an object of the present invention to provide an improved apparatus and method for inserting a vessel plug into the body of a living patient.

It is another object of the present invention to provide the aforementioned improved apparatus to include an expandable porous mesh which can be inserted directly within a blood vessel without significantly interrupting blood flow through the vessel while the apparatus is in use.

It is still another object of the present invention to provide the aforementioned improved apparatus and method for its use wherein the expandable mesh can assume one orientation during insertion and withdrawal of the apparatus and another orientation when a vessel plug is being inserted within the wound or incision to thereby prevent the plug from entering the blood vessel.

These and other objects of the present invention will be more fully appreciated by those skilled in the art following a consideration of the remainder of the disclosure including the drawings, the detailed description of the preferred embodiment and the appended claims.

DETAILED DESCRIPTION OF THE PREFERRED EMBODIMENT

Figure 1:
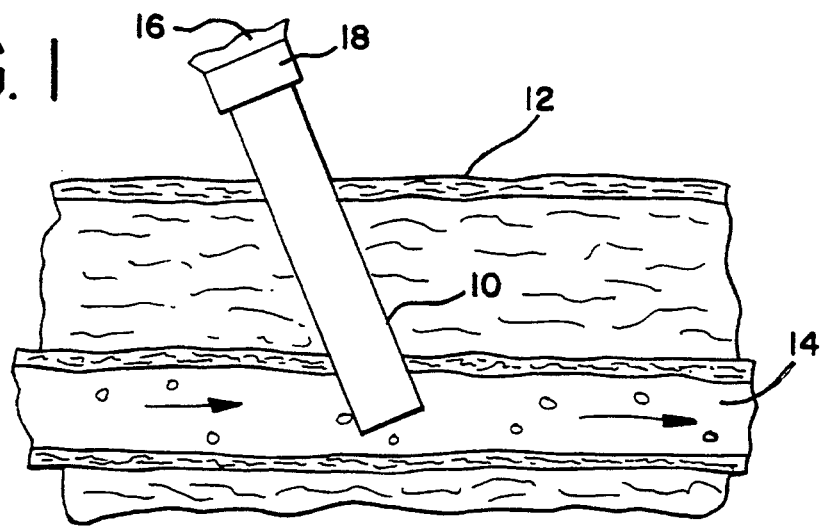
FIG. 1 is a fragmentary view, in schematic, of a sheath introducer extending through the skin of a live patient and into a blood vessel.

The present invention provides an apparatus and a method for its use. The apparatus of the invention is an expandable mesh catheter device wherein a porous balloon mesh is affixed to the end of a shaft or catheter for insertion within a wound in the body of a living patient. The mesh is configured for insertion within a blood vessel and may be expanded so that a surface of the expanded mesh can be positioned adjacent the inner lumen of the blood vessel contiguous with the wound or incision therein. A vessel plug is inserted within the wound and positioned so that the distal end of the plug is adjacent the expanded mesh. The expanded porous mesh is configured to allow blood to flow therethrough and to prevent the intrusion of the vessel plug into the blood vessel thereby avoiding possible occlusion, stenosis or thrombosis. Once the plug is properly positioned, the expanded mesh can be relaxed to its original condition and withdrawn from the wound, leaving the vessel plug to prevent further bleeding while coagulation takes place at the wound site.

In discussing the preferred embodiment of the invention, reference is now made to the various figures which depict an embodiment of the apparatus of the invention. Pertinent structural elements are labeled with reference numerals and like reference numerals are intended to indicate like structure.

Referring now to the various figures, FIG. 1 is a diagrammatic illustration of a sheath introducer 10 which has been inserted and advanced through the surface of the skin 12 of a living patient and into a blood vessel 14. The introducer 10 is provided with a release valve 16 at its proximal end 18. As is known by those skilled in the art, a guiding catheter, an angioplasty device or a medical device of another known use is typically inserted through the introducer 10 through the valve 16 and into the blood vessel 14, typically along a guidewire, to perform a specific medical procedure within the vessel. Once the procedure is completed, the device is typically withdrawn from the vessel 14 and back through the introducer 10. The sheath introducer 10 must also be removed, leaving a wound or opening in the blood vessel 14. While the blood in the blood vessel 14 will eventually coagulate to prevent further bleeding, the apparatus and method of the present invention can be utilized to stop excessive bleeding hasten blood coagulation and prevent significant bruising around the incision.

Figure 2:
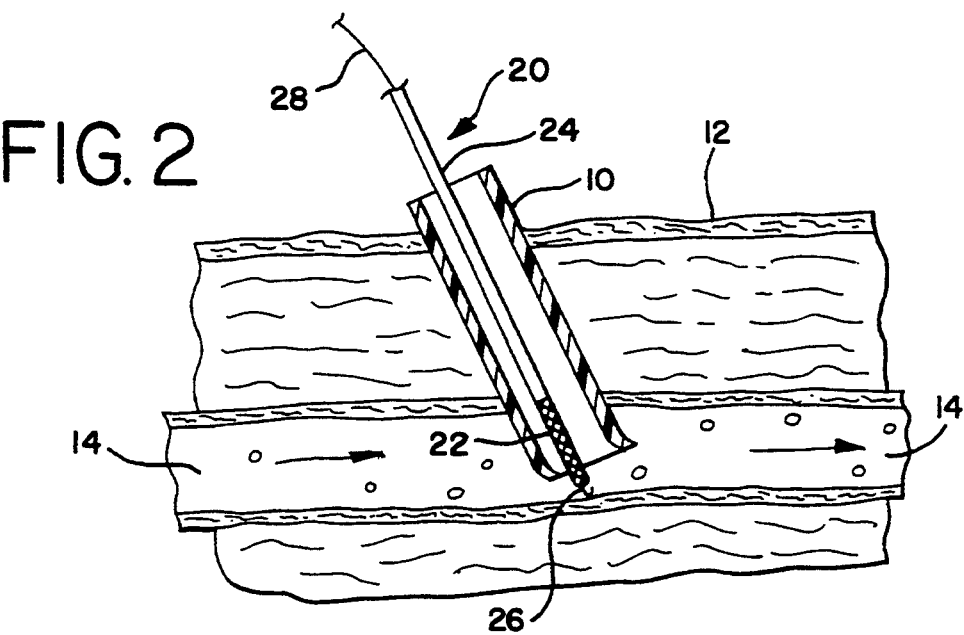
FIG. 2 is a side elevational view, in partial cross section, showing the apparatus of the present invention inserted into the patient through a sheath introducer.

FIG. 2 illustrates a preferred embodiment of the invention. The apparatus 20 includes an expandable mesh 22 affixed to the distal end of a catheter 24 and the device 20 is dimensioned to fit within the sheath introducer 10 to extend through the introducer and into a blood vessel 14. A guidewire with an atraumatic tip 26 may be used to assist in positioning the apparatus 20 in a known manner. A control wire 28 is affixed to the inner surface of the mesh 22 at the distal portion thereof and extends through the mesh 22 and the catheter 24 and can be connected to a suitable actuating mechanism such as those disclosed in U.S. Pat. Nos. 4,885,003 and 4,921,484, the disclosures of which are incorporated by reference hereinto.

Figure 3:
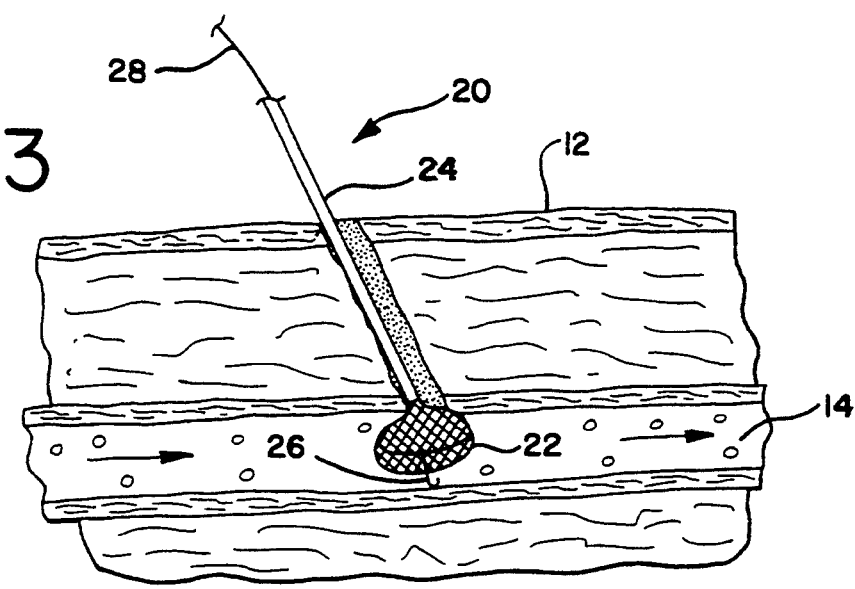
FIG. 3 is a side elevational view in partial cross section of the apparatus of the invention inserted through the sheath introducer and showing the expandable member in an expanded condition.

In operation, the device 20 is inserted into the body of the patient through the sheath introducer 10 and along a guidewire 26 into the blood vessel 14 so that the expandable mesh 22 is positioned directly within the blood vessel 14. Once the distal end of the device, including the mesh 22, is positioned within the vessel 14, the sheath introducer 10 can be withdrawn and the control wire 28 is pulled to thereby expand the expandable mesh 22, substantially as shown in FIG. 3. As shown, the proximal portion of the expanded mesh member 22 is positioned adjacent to the inner lumen of the blood vessel 14 contiguous with the wound or opening within the vessel. In one important aspect of the invention, the expandable mesh 22 is manufactured to be porous to allow for the continuous flow of blood through the vessel 14 and to thereby minimize occlusion of the blood vessel while the tip 22 of the device 20 is within the vessel 14.

The mesh 22 can be manufactured from pliable flexible wire such as stainless steel, for example or can also be manufactured from plastic materials or a combination of metal and plastic materials. Preferably, the mesh 22 is treated with an anti-thrombogenic agent which can include, for example, heparins, hirudin, hyaluronic acid and the like. The aforementioned antithrombogenic agents are merely illustrative and are not intended to be limiting in any way.

Figure 4:
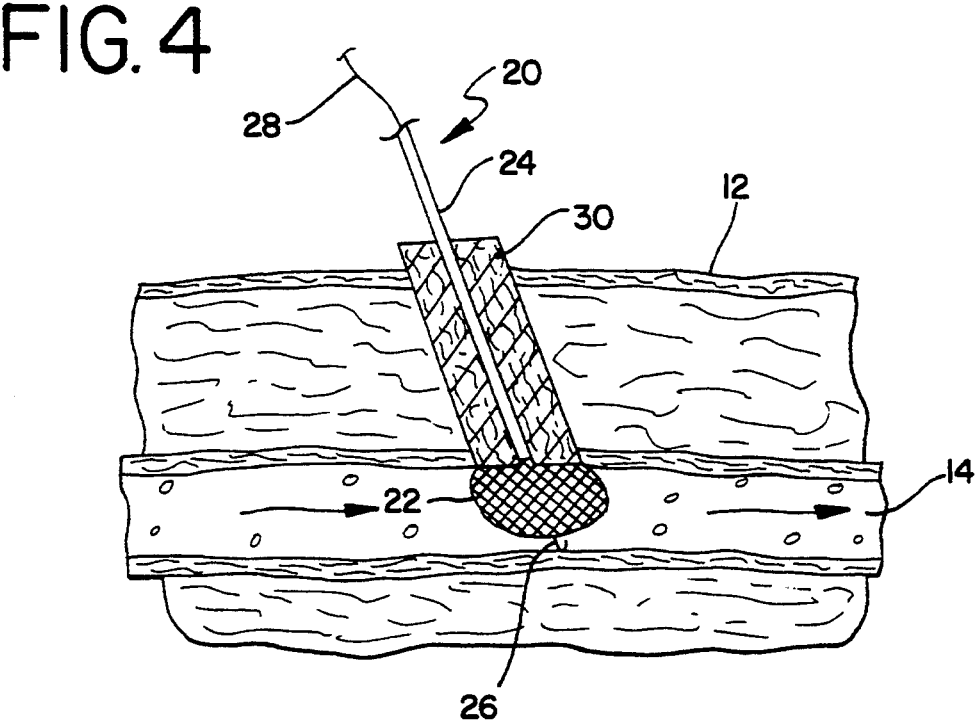
FIG. 4 is a side elevational view in partial cross section showing the apparatus of FIG. 3 and illustrating the vessel plug inserted within the wound or incision.

As illustrated in FIG. 4, a vessel plug 30 is provided for insertion into the incision or wound. The vessel plug 30 is a cylindrical member which is preferably constructed of a porous, biodegradable and expandable material such as a collagen sponge or a polymerized polylactic acid, or polyglycolic acid matrix or another suitable hemostatic material, as known to those skilled in the art.

The vessel plug 30 is inserted into the wound over the catheter 24 and advanced up to the vessel 14. When the plug 30 is advanced to the opening in the vessel 14, it is stopped from further advancement by the expanded mesh 22 which acts as an anchor to prevent the plug 30 from entering the vessel 14 while the plug is being positioned within the incision. The operator of the apparatus 20 can easily sense when the plug 30 is properly positioned within the wound or incision by noting its resistance to further advancement once the plug abuts the uppermost surface of the mesh 22. While the plug 30 is being positioned in the incision, blood flow through the vessel 14 is continuous and without substantial interruption because of the porous construction of the mesh 22. In this arrangement, the coagulation process can begin prior to the removal of the mesh 22 from the vessel 14. Since the plug 30 is prevented from being advanced into the vessel 14, possible stenosis or thrombosis at the site of the incision is avoided.

Figure 5:
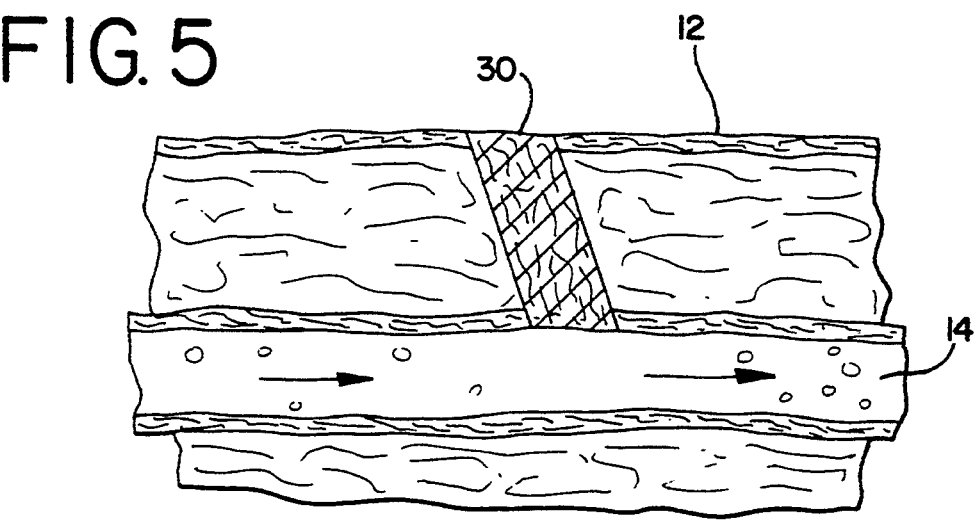
FIG. 5 is a side elevational view in cross section of the vessel plug inserted into the wound of the patient.

Once the plug 30 is positioned within the incision, tension on the control wire 28 can be released and the mesh 22 is allowed to relax and assume its original narrow profile so that the device 20 can be withdrawn while the plug 30 remains in place within the incision. FIG. 5 is illustrative of the plug 30 positioned within the incision following the removal of the device 20. The distal end 32 of the plug 30 is contiguous with the inner lumen of the blood vessel 14 without extending into the vessel. In this manner, the plug member 30 provides a suitable seal to prevent further bleeding through the incision and the positioning of the plug 30, as discussed herein, further avoids possible stenosis or thrombosis which could result if the plug were to extend or protrude into the vessel 14.

While a preferred embodiment of the present invention has been disclosed and described in detail herein, those skilled in the art will appreciate that various changes and modifications can be made to the disclosed embodiment without departing from the true spirit and scope of the invention, as further defined in the following claims.

WHAT IS CLAIMED IS:

1. An assembly for sealing or closing an incision or puncture in the body of a living patient wherein the incision or puncture extends into a blood vessel or an organ of the patient, the assembly comprising:
   an elongate shaft member having a proximal end and a distal end and having an expandable member disposed at said distal end, said expandable member constructed to be positioned alternatively in a relaxed condition and an expanded condition;
   said shaft member and said expandable member dimensioned to be inserted within the puncture so that said expandable member is positioned within a target organ or blood vessel of the patient and said expandable member is constructed to permit blood and other body fluids to pass therethrough;
   control means connected to said expandable member and associated with said shaft member for selectively positioning said expandable member between said expanded condition and said relaxed condition; and
   a vessel plug operatively associated with said shaft member for insertion into the puncture, said expandable member configured to cooperate with said plug when said expandable member is in said expanded condition to prevent said vessel plug from entering the vessel or the organ of the patient, and said vessel plug, when sealingly positioned within the puncture, extends from the skin of the patient to the target organ or blood vessel without extending into said vessel or said organ.

2. The assembly as defined in claim 1 wherein said elongate shaft member is a catheter and said expandable member is a tubular mesh of woven interlaced filaments.

3. The assembly as defined in claim 2 wherein said expandable member is treated with an antithrombogenic agent selected from the group consisting essentially of heparin, hirudin, hyaluronic acid, D-phenylalanyl-L-prolyl-L-arginine chloromethyl ketone and combinations thereof.

4. The assembly as defined in claim 1 wherein said control means is a wire member affixed to a distal portion within said expandable member and extending through said shaft, said wire member transferring an externally applied pulling force on said expandable member to position said expandable member in said expanded condition, said expandable member being constructed of a resilient material capable of assuming said relaxed condition when said pulling force of said wire member is released.

5. The assembly as defined in claim 1 wherein said vessel plug is a cylindrical rod constructed of a porous biodegradable material.

6. The assembly as defined in claim 5 wherein said plug is made of a substance selected from the group consisting essentially of collagen sponge, polylactic acid, polyglycolic acid matrix or combinations thereof.

7. The assembly as defined in claim 1 further comprising a sheath introducer having a lumen extending longitudinally therethrough, said introducer dimensioned to receive said shaft member and said expandable member within said lumen.

8. An apparatus for sealing or closing an incision or puncture in the body of a living patient wherein the incision or puncture extends into a blood vessel or an organ of the patient, the apparatus comprising:
   a catheter having a proximal end and a distal end and having an expandable member disposed at said distal end of said catheter, said expandable member constructed to be positioned alternatively in a relaxed condition and an expanded condition;
   said expandable member dimensioned to be positioned within a target organ or blood vessel of the patient and constructed to permit blood and other body fluids to pass therethrough;
   a control wire affixed at one end thereof to an inner portion of said expandable member and extending through said catheter, said control wire transferring an externally applied pulling force to said expandable member to position said expandable member in said expanded condition, said expandable member constructed to assume said relaxed condition when the pulling force applied to said control wire is released; and
   a vessel plug operatively associated with said catheter and said expandable member, said vessel plug dimensioned to close the puncture or incision, said expandable member, when in said expanded condition within said blood vessel or said target organ, preventing said vessel plug from extending into said vessel or said organ.

9. The apparatus of claim 8 wherein said vessel plug is a cylindrical rod constructed of a porous biodegradable material.

10. The apparatus of claim 9, wherein said vessel plug is made of a substance selected from the group consisting essentially of collagen sponge, polyactic acid, polyglycolic acid matrix or combinations thereof.

11. The apparatus of claim 8 further comprising a sheath introducer having a lumen extending longitudinally therethrough, said introducer dimensioned to receive said catheter and said expandable mesh within said lumen.

12. A method for sealing or closing an incision or puncture in the body of the living patient wherein the incision or puncture extends into a blood vessel or organ of the patient, the method comprising:
   inserting an elongated catheter into the incision, said elongated catheter having a distal end and a proximal end and having an expandable mesh disposed at said distal end, said expandable member constructed to be positioned alternatively in a relaxed condition and an expanded condition;
   expanding said expandable mesh within said blood vessel or said target organ and permitting blood or other body fluids to pass through the expandable mesh;
   positioning a surface of said expandable mesh adjacent the incision or purchase in said blood vessel or said target organ;
   inserting a vessel plug into said incision or puncture, said expandable mesh operating in said expanded condition to prevent said vessel plug from extending into said vessel or target organ of said patient;
   positioning said expandable mesh in said relaxed condition; and
   retracting said elongated catheter and said expandable mesh from said incision or puncture while retaining said vessel plug within said incision or puncture.

13. The method of claim 12 wherein said expanding of said expandable mesh is accomplished by exerting a pulling force on a control member affixed to an inner portion of said expandable mesh, said pulling force positioning said expandable mesh into said expanded condition.

14. The method of claim 12 wherein said inserting of an elongated catheter into the incision is accomplished by inserting said catheter through a sheath introducer extending from the skin of the patient and into said vessel or target organ.

15. The method of claim 12 wherein said inserting of said vessel plug includes providing said plug as a cylindrical member made of a porous biodegradable material; and inserting said plug in said wound or incision to contact said surface of said mesh adjacent the incision.

16. The method of claim 15 wherein said vessel plug is provided as a collagen sponge, a rod of polymerized polylactic acid or a polyglycolic acid matrix.

17. The method of claim 12 further comprising treating said catheter and said expandable mesh with an antithrombogenic agent.

18. The method of claim 17 wherein said anti-thrombogenic agent is selected from the group consisting essentially of heparin, hirudin, hyaluronic acid, D-phenylalanyl-L-prolyl-L-arginine chloromethyl ketone and combinations thereof.

* * * * *

UNITED STATES PATENT AND TRADEMARK OFFICE
CERTIFICATE OF CORRECTION

PATENT NO. : 5,370,660
DATED      : December 6, 1994
INVENTOR(S): Lawrence A. Weinstein and Richard A. Hillstead It is certified that error appears in the above-indentified patent and that said Letters Patent is hereby corrected as shown below:

Col. 1, line 37, insert --of-- before "the vessel".
Col. 4, line 8, insert a comma --,-- after "bleeding".
Col. 6, line 64, "polyactic" should read --polylactic--.

Signed and Sealed this

Fifth Day of December, 1995

Attest:

BRUCE LEHMAN

*Attesting Officer*  *Commissioner of Patents and Trademarks*